(12) United States Patent
Patel et al.

(10) Patent No.: US 11,433,058 B2
(45) Date of Patent: Sep. 6, 2022

(54) NON-PULSATILE PROLONGED-RELEASE BETAHISTINE ORAL SOLID COMPOSITIONS

(71) Applicant: INTAS PHARMACEUTICALS LTD., Ahmedabad (IN)

(72) Inventors: Himanshukumar Dasharathlal Patel, Ahmedabad (IN); Vinod Purushottam Dube, Ahmedabad (IN); Venkataramana Naidu, Ahmedabad (IN); Sunil Shantwan Borude, Ahmedabad (IN)

(73) Assignee: INTAS PHARMACEUTICALS LTD., Ahmedabad (IN)

( * ) Notice: Subject to any disclaimer, the term of this patent is extended or adjusted under 35 U.S.C. 154(b) by 194 days.

(21) Appl. No.: 16/632,500

(22) PCT Filed: Jul. 16, 2018

(86) PCT No.: PCT/IB2018/055233
§ 371 (c)(1),
(2) Date: Jan. 20, 2020

(87) PCT Pub. No.: WO2019/016668
PCT Pub. Date: Jan. 24, 2019

(65) Prior Publication Data
US 2021/0161871 A1  Jun. 3, 2021

(30) Foreign Application Priority Data
Jul. 20, 2017  (IN) .............................. 201721025857

(51) Int. Cl.
*A61K 9/20* (2006.01)
*A61K 31/4402* (2006.01)
*A61K 9/00* (2006.01)

(52) U.S. Cl.
CPC ........ *A61K 31/4402* (2013.01); *A61K 9/0053* (2013.01); *A61K 9/205* (2013.01); *A61K 9/2009* (2013.01); *A61K 9/2013* (2013.01); *A61K 9/2054* (2013.01); *A61K 9/2072* (2013.01); *A61K 9/2095* (2013.01)

(58) Field of Classification Search
None
See application file for complete search history.

(56) References Cited

U.S. PATENT DOCUMENTS

| 2003/0157167 A1* | 8/2003 | Kao | ........................ A61K 47/36 424/468 |
| 2007/0003618 A1 | 1/2007 | Lenaerts | |

FOREIGN PATENT DOCUMENTS

| EP | 1493435 | 1/2005 | |
| WO | WO-0053162 A1 * | 9/2000 | ............. A61P 25/00 |
| WO | 2012131722 A1 | 10/2012 | |
| WO | 2014001267 A2 | 1/2014 | |
| WO | 2014001267 A3 | 1/2014 | |

OTHER PUBLICATIONS

Kovshel A. Yu. et al, "sustained release betahistine tablets: elaboration of their composition and technology", Pharmacy, 2014, vol. 6, pp. 40, including English Translation.
Shuang He et al. ": Formulation and evaluation of novel coating flating tables of bergenin and cetirizine dihydrochloride for gastric delivery". Drug Development and Industrial Pharmacy. Oct. 1, 2012, pp. 1280-1288.
International Search Report for PCT/IB2018/055233, dated Oct. 9, 2018, 1 page.
Radu Cazacincu et. al., "The optimization of prolonged release matrix tablets with betahistine dihydrochloride—Part I", Farmacia, 2011, vol. 59, 2, 209-215. abstract, table 1, table 3, p. 211.

* cited by examiner

*Primary Examiner* — Susan T Tran
(74) *Attorney, Agent, or Firm* — Brooks Kushman P. C.

(57) ABSTRACT

An oral solid non-pulsatile 24 hours prolonged-release composition including an amount of betahistine, or of a pharmaceutically acceptable salt thereof, equivalent to 48 mg of betahistine dihydrochloride, together with one or more pharmaceutically acceptable excipients or carriers, wherein the composition exhibits a dissolution profile according to which: up to 30% by weight of betahistine is dissolved in 1 hour; from 35% to 45% by weight of betahistine is dissolved in 2 hours; from 46% to 60% by weight of betahistine is dissolved in 4 hours; from 61% to 80% by weight of betahistine is dissolved in 8 hours; from 81% to 97% by weight of betahistine is dissolved in 16 hours; and from 98% to 100% by weight of betahistine is dissolved in 24 hours. It also relates to the treatment of a vestibular disease or condition, more particularly in the treatment of Ménière's disease.

12 Claims, 1 Drawing Sheet shows the mean plasma concentration (MPC) for 24 hours after a unique oral administration of the composition of Example 1 of the present invention having 48 mg of betahistine dihydrochloride. MPC stands for mean plasma concentration (ng/mL) and T refers to time expressed in hours.

NON-PULSATILE PROLONGED-RELEASE BETAHISTINE ORAL SOLID COMPOSITIONS

CROSS-REFERENCE TO RELATED APPLICATION

This application is the U.S. national phase of PCT Application No. PCT/M2018/055233 filed on Jul. 16, 2018, which claims priority to IN Patent Application No. IN201721025857 filed on Jul. 20, 2017, the disclosures of which are incorporated in their entirety by reference herein.

FIELD OF THE INVENTION

The present invention relates to an oral solid non-pulsatile prolonged-release composition of betahistine. Particularly, to a non-pulsatile 24 hours prolonged-release oral solid composition having an amount of betahistine, or of a pharmaceutically acceptable salt thereof, equivalent to 48 mg of betahistine dihydrochloride. It also relates to a process for its preparation and its use in therapy, especially in the treatment of a vestibular disease or condition more particularly in the treatment of Ménière's disease.

BACKGROUND OF THE INVENTION

Betahistine is the International Nonproprietary Name (INN) of N-methyl-2-(pyridin-2-yl)ethanamine having the CAS number 5638-76-6. The structure of betahistine corresponds to the formula (I)

Betahistine is a vasodilator agent which is commonly used as its dihydrochloride salt. After oral administration, betahistine dihydrochloride is almost completely absorbed from all parts of the gastro-intestinal tract and, after absorption; betahistine dihydrochloride is rapidly and almost completely metabolized into its metabolite 2-pyridylacetic acid (2-PAA).

The first marketing authorization in Europe for betahistine dihydrochloride was in 1970 for balancing or alleviating vertigo, tinnitus, hearing loss and nausea symptoms associated with Ménière's disease. The treatment of Ménière's disease is a long-term treatment which encompasses a first initial oral treatment phase followed by a second maintained phase. Particularly, the first initial treatment phase involves the oral administration of 8-16 mg of betahistine dihydrochloride three times per day; meanwhile the second maintained treatment phase involves the oral administration of 24-48 mg of betahistine dihydrochloride without exceeding a total daily dose of 48 mg.

Betahistine dihydrochloride is commercially available in form of immediate release tablets of 8 mg, 16 mg or 24 mg or in form of oral solution of 8 mg/ml. Therefore, the indicated posology for the treatment of Ménière's disease encompasses two to four oral intakes per day depending on the dosage form. Thus, the most important factor that compromises the efficacy of the treatment of Ménière's disease with betahistine dihydrochloride for the last 40 years is the drug compliance of the patient.

Therefore, various attempts have been made to improve the drug compliance by reducing the frequency of daily intakes maintaining the plasma levels of the active ingredient for a long period of time.

It is well known in the state of the art that the use of matrix-based compositions can determine the resorption of active ingredients and therefore, its release from the matrix-based composition. Particularly, monolithic prolonged-release matrix-based compositions having from 12 mg to 48 mg of betahistine hydrochloride have been disclosed in the state of the art. Particularly, Kovshel A. Yu. et al. discloses sustained-release matrix-based compositions containing 48 mg of betahistine dihydrochloride. These compositions are mainly based on a matrix formed by povidone and polyvinyl acetate in combination with microcrystalline cellulose and calcium hydrophosphate as excipients. After the single-dose administration of these sustained-released compositions, betahistine hydrochloride is released from the composition for 12 hours. Unfortunately, the premature and exaggerated release of the active ingredient from these compositions (i.e. dose-dumping effect) cannot be avoided. In particular, about 40% of betahistine dihydrochloride was released from the composition after 1 hour of administration and about 60% after 2 hours. This dose-dumping effect can cause a greatly increase in the concentration of the active ingredient in the body, producing fluctuations in its plasma concentration and therefore, adverse effects associated with both infra- and/or over-dosing. Thus, the administration of these compositions does not maintain the release for a sufficiently long time for being administered once-daily, which means that there is still required two or more intakes of these compositions for having therapeutically effective amount of betahistine dihydrochloride during 24 hours (cf. Kovshel A. Yu. et al, "sustained release betahistine tablets: elaboration of their composition and technology", Pharmacy, 2014, vol. 6, pp. 40).

In this sense, PCT patent application WO2014001267 discloses that the use of sustained matrix-based compositions are useful for controlling the release of those active ingredients that have bad solubility and/or are not hydroscopic. However, considerable difficulties arise with respect to control the release of hygroscopic active ingredients which at the same time highly soluble. PCT patent application WO2014001267 points out that this is the case of Betahistine dihydrochloride, that can be considered as a highly water-soluble (water solubility of 49.3 mg/mL) and also hygroscopic active ingredient.

Furthermore, WO2014001267 also indicates that additional difficulties arise in the modification of the release profile of such active ingredient due to its acidic properties. Namely, the high acidity of betahistine can attack and/or decomposes the excipients or carriers of the formulation and then can modify (alter) the release of the active ingredient.

To sum up, PCT patent application WO2014001267 discloses that due to the high solubility, hygroscopicity and acidic properties of betahistine, it is practically impossible to control its release by exclusively using a common non-pulsatile matrix-based retardant formulation as defined above. Therefore, WO2014001267 provides a more feasible approach for prolonging the release of betahistine dihydrochloride and therefore, reducing the frequency of drug dose intakes. This approach is focused on the use of a multi-particulate pulsed prolonged release matrix based-composition which provides a first immediate release of a first portion of the active ingredient just after the drug intake and a retardant release of a second portion of the active ingredient. In fact, these pulsed compositions simulate (mimic) the intake of two dosage forms per day instead of providing a unique non-pulsed dosage form having a prolonged-release of the active ingredients.

Particularly, PCT patent application WO2014001267 discloses a core-shell pulsed prolonged-release composition containing 24 mg of betahistine dihydrochloride. The composition comprises a retardant-released core having 12 mg of betahistine dihydrochloride and an external immediate-released shell containing the remaining 12 mg of active ingredient.

However, again due to the high solubility and hygroscopicity of the active ingredient, it is still difficult to achieve a sufficient temporal separation between the first immediate release pulse of betahistine (from the shell) and the second retardant release pulse of betahistine (from the core) by the exclusively use of the retardant matrix-based core. Then, an intermediate film-coating between the core and the shell is commonly required. Thereby, these compositions still produce fluctuations in the plasma concentration of the active ingredient and hence the adverse effects associated with both infra- and/or over-dosing are still maintained.

Therefore, from what is known in the art it is derived that there is a long need of providing stable oral 24 hours prolonged-release compositions containing an amount of betahistine, or of a pharmaceutically acceptable salt thereof, equivalent to 48 mg of betahistine dihydrochloride, which may be suitable for once-daily administration without having side effects associated with fluctuations in plasma concentration of the active ingredient.

SUMMARY OF THE INVENTION

The inventors, despite the teaching-away comments from WO2014001267, have surprisingly found a non-pulsatile prolonged-release oral solid composition comprising an amount of betahistine, or of a pharmaceutically acceptable salt thereof, equivalent to 48 mg of betahistine dihydrochloride, that exhibits an appropriate dissolution profile which may be suitable for maintaining the therapeutically effective plasma concentration of betahistine parent drug and main metabolite 2-PAA (absolute bioavailability about 99%), for up to 24 hours.

The once-daily administration of the oral solid composition of the present invention exhibits a lower maximum blood concentration (Cmax) and a higher minimum blood concentration (Cmin) of betahistine, and also of betahistine metabolite 2-PAA, as compared to the twice-daily administration of an immediate release oral solid composition, which reduces its plasma concentration fluctuation and therefore, avoids infra-dosing or over-dosing side effects associated with the administration of at least two immediate unique dosage forms or a unique multi-particulate dosage form containing an immediate and retardant release dosage forms.

Furthermore, the inventors have also surprisingly found that the total drug exposure exhibited after the once-daily administration of the composition of 48 mg of betahistine dihydrochloride of the present invention is bioequivalent to the total drug exposure obtained after twice-daily administration of an immediate release composition of 24 mg of betahistine dihydrochloride. It means that the composition of 48 mg of betahistine dihydrochloride of the present invention (once daily) shows comparable pharmacokinetic parameters on bioavailability (e.g. $C_{max}$, $AUC_{0-t}$, $AUC_{0-\infty}$, $AUC_{0-\tau,ss}$, $C_{max,\,ss}$, and $C_{mm,\,ss}$) of betahistine, and of betahistine metabolite 2-PAA, to that of betahistine dihydrochloride immediate release formulation (taken twice daily), as set out in the European medicines Agency (EMA) "Guideline on the pharmacokinetic and clinical evaluation of modified release dosage forms" (EMA/CPMP/EWP/280/96Corr1). Thereby, the compositions of the present invention can be considered equivalent to twice-daily administration of the immediate release composition according to the guidelines on modified release formulations of the European medicines Agency (EMA).

Besides, the high-dosed prolonged-release composition of the present invention also shows a good stability of the active ingredient even though its high water solubility, high hygroscopicity and high acidity. Particularly, the compositions of the present invention comply with the strict criteria of impurities limit specifications required by the medicine regulatory agencies.

Furthermore, the composition of the present invention, which comprises betahistine or a pharmaceutically salt thereof equivalent to 48 mg of betahistine dihydrochloride, allows simplifying the dose posology by the reduction of daily intakes to once-daily administration. It is advantageous because it allows improving the treatment compliance by offering improved convenience to patients, therefore leading to increased patient adherence and treatment effectiveness.

The release profile of the compositions of the invention also allow maintaining the therapeutically effective amount of betahistine, or a pharmaceutically acceptable salt thereof, equivalent to 48 mg of betahistine dihydrochloride, for 24 hours and even at a prolonged period of time after several days of administration (i.e. multiple dose steady-state) with once a day dosing without side effects associated to dose accumulation. Also, the composition of the invention leads to improved tolerability by means of lesser fluctuations between the peak and trough plasma concentrations due to the steady-state release of the drug over a prolonged period of time.

Thus, a first aspect of the present invention relates to a non-pulsatile 24 hours prolonged-release oral solid composition comprising an amount of betahistine, or of a pharmaceutically acceptable salt thereof, equivalent to 48 mg of betahistine dihydrochloride, together with one or more pharmaceutically acceptable excipients or carriers, wherein the composition exhibits a dissolution profile according to which: up to 30% by weight of betahistine is dissolved in 1 hour; from 35% to 45% by weight of betahistine is dissolved in 2 hours; from 46% to 60% by weight of betahistine is dissolved in 4 hours; from 61% to 80% by weight of betahistine is dissolved in 8 hours; from 81% to 97% by weight of betahistine is dissolved in 16 hours; and from 98% to 100% by weight of betahistine is dissolved in 24 hours, wherein the dissolution profile is measured using a USP type I apparatus (basket), placing the composition in 900 mL of phosphate buffer having pH 6.8, at 37° C. and 100 rpm. The said oral solid composition of the invention has proved to show an essentially similar dissolution profile under the different pH physiological conditions. Namely, it exhibits essentially the same dissolution profile described above when measured under the same conditions above, but in 0.1N hydrochloric acid or in acetate buffer having pH 4.5, instead of phosphate buffer.

A second aspect of the invention relates to a process for the preparation of the composition as defined in the first aspect of the invention which comprises: (a) preparing a solution of betahistine or a pharmaceutically acceptable salt thereof in a polar solvent selected from the group $(C_1-C_4)$ alkyl-CO—$(C_1-C_4)$alkyl, $(C_1-C_4)$alky)-COO—$(C_1-C_4)$alkyl, water and mixture thereof; (b) sifting and mixing one or more diluents, one or more stabilizers and optionally one or more binders to obtain a mixture; (c) granulating the mixture of step (b) by the addition of the solution of step (a) to obtain wet granules; (d) drying the wet granules obtained in step (c) to obtain dried granules; (e) mixing the dried granules obtained in step (d) with one or more hydrophilic matrix forming agents to obtain a mixture; (f) optionally, blending the mixture obtained in step (e) with one or more of the excipients or carriers selected from the group consisting of glidant and lubricant to obtain a mixture; (g) compressing the mixture obtained in step (f) to form tablets; and (h) optionally, coating the tablets obtained in step (g).

It is also part of the invention the composition of the first aspect of the invention for use in therapy; and the composition of the first aspect of the invention, for use in the treatment of a vestibular disease or condition, preferably for use in the treatment of vertigo, tinnitus, hearing loss and nausea associated with Ménière's syndrome.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges given, such as temperatures, times, weights, and the like, should be considered approximate, unless specifically stated.

The terms "percentage (%) by weight", "weight/weight %" and "w/w %" have the same meaning and are used interchangeable. They refer to the percentage of each ingredient of the composition in relation to the total weight of the composition.

The term "weight ratio" refers to the relation in weight of a given compound to another given compound, for instance, between the hydroxypropylmethylcellulose and the carrageenan.

The term "room temperature" refers to a temperature of the environment, without heating or cooling, and is generally from 20° C. to 25° C.

The terms "under fed conditions" or "fed state" as used herein mean that the pharmacokinetic parameters have been measured when the composition of betahistine or of a pharmaceutically acceptable salt thereof of the present invention is administered orally to a human concomitantly with food or just after the ingestion of food, as compared to the "fasted state" or "under fasted conditions", which means that the pharmacokinetic parameters have been measured when the composition of betahistine of the present invention is administered orally to a human without food.

The term "alkyl" refers to a saturated straight or branched hydrocarbon chain which contains the number of carbon atoms specified in the description or claims. Examples include, among others, the group methyl, ethyl, propyl, isopropyl, butyl, isobutyl, sec-butyl, and tert-butyl.

As it is mentioned above, the first aspect of the present invention relates to a non-pulsatile 24 hours prolonged-release composition comprising an amount of betahistine, or of a pharmaceutically acceptable salt thereof, equivalent to 48 mg of betahistine dihydrochloride, together with one or more pharmaceutically acceptable excipients or carriers, wherein the composition exhibits the above-mentioned target dissolution profile.

The terms "pulsatile", "pulsatile-release" or "pulsed" have the same meaning and are used interchangeable. They refer to the release profile in which at least two discrete quantities of the active ingredient are released at spaced apart time intervals which results in at least two distinct plasma concentration peaks. And, the term "non-pulsatile" release refers to the release profile in which the total amount of the active ingredient is released in a unique pulse which results in only one plasma concentration peak.

In the context of the present invention, the term "prolonged release" refers to a composition in which the rate of release of the active ingredient from the formulation after administration has been reduced. In other words, it is a composition exhibiting a slower release of the active agent than that of a conventional immediate release pharmaceutical composition administered by the same route. In general, the term "prolonged release dosage form" refers to that the active ingredient is released from the pharmaceutical dosage form over an extended period of time and not in an immediate release (cf. Quality of prolonged release oral solid dosage forms Directive 75/318/EEC October 1992. Section 3AQ19a pp. 167-174). In the context of the present invention "prolonged release" means that betahistine or a pharmaceutically acceptable salt thereof is released from the composition over an extended period of time of 24 hours. Particularly, for the purposes of the present invention, the term "prolonged release" refers to a composition that exhibits a dissolution profile according to which: up to 30% by weight of betahistine is dissolved in 1 hour; from 35% to 45% by weight of betahistine is dissolved in 2 hours; from 46% to 60% by weight of betahistine is dissolved in 4 hours; from 61% to 80% by weight of betahistine is dissolved in 8 hours; from 81% to 97% by weight of betahistine is dissolved in 16 hours; and from 98% to 100% by weight of betahistine is dissolved in 24 hours, wherein the dissolution profile is measured using a USP type I apparatus (basket), placing the composition in 900 mL of 0.1N hydrochloric acid, or of acetate buffer having pH 4.5, or of phosphate buffer having pH 6.8, at 37° C. and 100 rpm.

The composition of the invention comprises betahistine or a pharmaceutically acceptable salt thereof. In an embodiment, the composition of the invention comprises betahistine free base equivalent to 48 mg of betahistine dihydrochloride. In an embodiment, the composition of the invention is one wherein the betahistine is in form of a pharmaceutically acceptable salt thereof equivalent to 48 mg of betahistine dihydrochloride. The term "pharmaceutically acceptable salt" used herein encompasses a salt formed from pharmaceutically acceptable non-toxic acids including inorganic or organic acids. There is no limitation regarding the salts, except that if used for therapeutic purposes, they must be pharmaceutically acceptable. Salts of betahistine may be prepared from pharmaceutically acceptable non-toxic acids, including inorganic and organic acids. Such acids include among others acetic, benzene sulfonic, benzoic, camphor sulfonic, citric, ethansulfonic, fumaric, gluconic, glutamic, hydrobromic, hydrochloric, lactic, maleic, malic, mandelic, methanesulfonic, phosphoric, succinic, sulphuric, tartaric, and p-toluensulfonic acid. In an embodiment, the betahistine is in form of betahistine dihydrochloric acid salt, i.e. betahistine dihydrochloride.

The composition of the first aspect of the invention comprises an amount of betahistine, or of a pharmaceutically acceptable salt thereof, equivalent to 48 mg of betahistine dihydrochloride; preferably comprises 48 mg of betahistine dihydrochloride. When the value of the amount of betahistine or a pharmaceutically acceptable salt is given it is said that this is an "approximate" value due to the measurement error. It should be understood that when an amount of 48 mg is mentioned, it corresponds to the amount ±0.5, which means from 47.5 mg to 48.5 mg. The variability of the results is due to the inherent sensibility of the used analytical instrument for analysis.

In an embodiment, the betahistine, or a pharmaceutically acceptable salt thereof, equivalent to 48 mg of betahistine dihydrochloride has such degree of purity which is required by the regulatory authorities for being used as active ingredient. In an embodiment, the betahistine, or a pharmaceutically acceptable salt thereof, equivalent to 48 mg of betahistine dihydrochloride has a chemical purity equal to or higher than 98 area % measured by HPLC; preferably, equal to or higher than 99 area % measured by HPLC.

Conditions of the HPLC analysis:
Flux: 1.5 mL/min
Column: Zorbax Eclipse XDB C18 (150 mm×4.6 mm) 5μ, Make: Agilent
Porous size of the column: 5μ
Phases: Buffer:ACN (60:40)
Column temperature: 35° C.
Injection volume: 15 μL
Detection wavelength: 260 nm
Gradient: NA
Isocratic: Buffer:ACN (60:40)

In an embodiment, the betahistine, or a pharmaceutically acceptable salt thereof, equivalent to 48 mg of betahistine dihydrochloride is a crystalline form.

In an embodiment, the non-pulsatile 24 hours prolonged-release oral solid composition of the present invention exhibits a dissolution profile according to which: up to 30% by weight of betahistine is dissolved in 1 hour; from 35% to 45% by weight of betahistine is dissolved in 2 hours; from 46% to 60% by weight of betahistine is dissolved in 4 hours; from 61% to 80% by weight of betahistine is dissolved in 8 hours; from 81% to 95% by weight of betahistine is dissolved in 16 hours; and from 98% to 100% by weight of betahistine is dissolved in 24 hours, wherein the dissolution profile is measured using a USP type I apparatus (basket), placing the composition in 900 mL of 0.1N hydrochloric acid, or of acetate buffer having pH 4.5, or of phosphate buffer having pH 6.8, at 37° C. and 100 rpm.

In an embodiment, the non-pulsatile 24 hours prolonged-release oral solid composition of the present invention exhibits a dissolution profile according to which: up to 30% by weight of betahistine is dissolved in 1 hour; from 35% to 40% by weight of betahistine is dissolved in 2 hours; from 46% to 58% by weight of betahistine is dissolved in 4 hours; from 61% to 78% by weight of betahistine is dissolved in 8 hours; from 81% to 95% by weight of betahistine is dissolved in 16 hours; and from 98% to 100% by weight of betahistine is dissolved in 24 hours, wherein the dissolution profile is measured using a USP type I apparatus (basket), placing the composition in 900 mL 0.1N hydrochloric acid, or of acetate buffer having pH 4.5, or of phosphate buffer having pH 6.8, at 37° C. and 100 rpm.

In an embodiment, after an oral single-dose administration of the composition under fed conditions, betahistine, or a pharmaceutically acceptable salt thereof, equivalent to 48 mg of betahistine dihydrochloride exhibits a maximum plasma concentration (Cmax) of from 400 ng/ml to 700 ng/ml expressed as plasma concentration of its 2-pyridylacetic acid (2-PAA) metabolite. In a preferred embodiment, after an oral single-dose administration of the composition under fed conditions, betahistine, or a pharmaceutically acceptable salt thereof, equivalent to 48 mg of betahistine dihydrochloride exhibits a maximum plasma concentration (Cmax) of from 500 ng/ml to 600 ng/ml expressed as plasma concentration of its 2-pyridylacetic acid metabolite. In a more preferred embodiment, after an oral single-dose administration of the composition under fed conditions, betahistine, or a pharmaceutically acceptable salt thereof, equivalent to 48 mg of betahistine dihydrochloride exhibits a maximum plasma concentration (Cmax) of from 530 ng/ml to 570 ng/ml expressed as plasma concentration of its 2-pyridylacetic acid metabolite. The term "Cmax" refers to the maximum concentration of betahistine2-PAA metabolite in the blood following an oral single-dose administration of the composition under fed conditions.

In an embodiment, after an oral single-dose administration of the composition under fed conditions, betahistine, or a pharmaceutically acceptable salt thereof, equivalent to 48 mg of betahistine dihydrochloride exhibits a time to maximum plasma concentration (Tmax) of from 5 h to 7 h expressed as plasma concentration of its 2-pyridylacetic acid (2-PAA) metabolite. In a preferred embodiment, after an oral single-dose administration of the composition under fed conditions, betahistine, or a pharmaceutically acceptable salt thereof, equivalent to 48 mg of betahistine dihydrochloride exhibits a time to maximum plasma concentration (Tmax) of from 5 h to 6 h expressed as plasma concentration of its 2-pyridylacetic acid metabolite. In a particular preferred embodiment, after an oral single-dose administration of the composition under fed conditions, betahistine, or a pharmaceutically acceptable salt thereof, equivalent to 48 mg of betahistine dihydrochloride exhibits a time to maximum plasma concentration (Tmax) of from 5.2 h to 5.6 h expressed as plasma concentration of its 2-pyridylacetic acid metabolite. The term "Tmax" refers to the time in hours when Cmax is achieved following an oral single-dose administration of the composition of the present invention under fed conditions.

In an embodiment, after an oral single-dose administration of the composition under fed conditions, betahistine, or a pharmaceutically acceptable salt thereof, equivalent to 48 mg of betahistine dihydrochloride exhibits an area under the time/plasma concentration curve from time 0 to 24 hours (AUC (0-24)) of from 5000 ng·h/ml to 10000 ng·h/ml expressed as plasma concentration of its 2-pyridylacetic acid metabolite. In a preferred embodiment, after an oral single-dose administration of the composition under fed conditions, betahistine, or a pharmaceutically acceptable salt thereof, equivalent to 48 mg of betahistine dihydrochloride exhibits an area under the time/plasma concentration curve from time 0 to 24 hours (AUC (0-24)) of from 6000 ng·h/ml to 8000 ng·h/ml expressed as plasma concentration of its 2-pyridylacetic acid metabolite. In a more preferred embodiment, after an oral single-dose administration of the composition under fed conditions, betahistine, or a pharmaceutically acceptable salt thereof, equivalent to 48 mg of betahistine dihydrochloride exhibits an area under the time/plasma concentration curve from time 0 to 24 hours (AUC (0-24)) of from 6500 ng·h/ml to 7500 ng·h/ml expressed as plasma concentration of its 2-pyridylacetic acid metabolite. The term "AUC" refers to the area under the time/plasma concentration curve after an oral single-dose administration of the composition of the present invention. AUC0-infinity denotes the area under the plasma concentration versus time curve from time 0 to infinity and $AUC_{0-t}$ denotes the area under the plasma concentration versus time curve from time 0 to time t.

In an embodiment, after an oral single-dose administration of the composition under fed conditions, betahistine, or a pharmaceutically acceptable salt thereof, equivalent to 48 mg of betahistine dihydrochloride exhibits a half-life (T½) from 8 h to 10 h expressed as plasma concentration of its 2-pyridylacetic acid metabolite. In a preferred embodiment, after an oral single-dose administration of the composition under fed conditions, betahistine, or a pharmaceutically acceptable salt thereof, equivalent to 48 mg of betahistine dihydrochloride exhibits a half-life (T½) from 8.5 h to 9.5 h expressed as plasma concentration of its 2-pyridylacetic acid metabolite. The term "half-life (T½)" refers to the time taken by betahistine 2-pyridylacetic acid metabolite (2-PAA) to lose half of its pharmacological activity.

The values of pharmacokinetic parameters after a single-unique dose of the composition of the invention as mentioned above (i.e. $C_{max}$, $C_{min}$, Tmax, $AUC_{0-t}$, $AUC_{0-\infty}$) as well as the simulated pharmacokinetic parameters after the multiple regimen of a single-unique dose of the composition of the invention at steady state (cf. values of $AUC_{0-\tau,ss}$, $C_{max, ss}$, and $C_{min,ss}$ in Example 5) indicate that, when administered as either single-dose or multiple-dose (steady state) under fed conditions, the once-daily administration of the oral solid composition of the present invention exhibits a lower maximum blood concentration (Cmin) and a higher minimum blood concentration (Cmax) of betahistine metabolite 2-PAA as compared to the twice-daily administration of an oral solid immediate release composition. Likewise, similar pharmacokinetic behaviour (e.g. in Cmax and Cmin) will be expected for the blood concentration of betahistine parent drug, which shows approximately 1% of absolute bioavailability. Further, the value of AUC, which represents the total drug exposure exhibited after the once-daily administration of the composition of the present invention, is bioequivalent to the total drug exposure obtained after twice-daily administration of the immediate release composition. Thereby, the compositions of the present invention can be considered equivalent to twice-daily administration of the immediate release composition according to the European medicines Agency (EMA) "Guideline on the pharmacokinetic and clinical evaluation of modified release dosage forms" (cf. EMA/CPMP/EWP/280/96Corr1). The 90% confidence interval for the ratio of pharmacokinetic parameters of the composition of the present invention and the comparative composition falling outside the scope of the present invention is contained within the acceptance interval of 80.00-125.00% according to the EMA Guideline on the investigation of bioequivalence (CPMP/EWP/QWP/1401/98 Rev. 1/Con, 2010).

In an embodiment, the composition of the present invention is one wherein the pharmaceutically acceptable excipients or carriers comprise one or more hydrophilic matrix forming agents. The term "hydrophilic matrix forming agent" refers to a pharmaceutical acceptable excipient or carrier that generates a gel in contact with water, and therefore, acts as a water hydrophilic dispersible rate-controlling polymer.

In an embodiment, the composition of the present invention is one wherein the one or more hydrophilic matrix forming agents is in an amount from 20% to 85% by weight with respect to the total weight of the composition. In an embodiment, the composition of the present invention is one wherein the one or more hydrophilic matrix forming agents is in an amount from 35% to 65% by weight with respect to the total weight of the composition. In a particular embodiment, the composition of the present invention is one wherein the one or more hydrophilic matrix forming agents is in an amount from 40% to 60%, preferably from 45% to 55%, and more preferably from 50% to 55%, by weight with respect to the total weight of the composition.

In an embodiment, the composition of the present invention is one wherein the pharmaceutically acceptable excipients or carriers comprise one or more hydrophilic matrix forming agents selected from the group consisting of cellulose derivatives, noncellulose polysaccharides; polyvinylpyrrolidone; polyvinylacetate; polyvinyl alcohol; polyacrylic acid; hyaluronic acid, a salt of hyaluronic acid; polyethylene oxide; and mixtures thereof.

In an embodiment, the composition of the present invention is one wherein the pharmaceutically acceptable excipients or carriers comprise one or more cellulose derivative being cellulose ether selected from the group consisting of methyl cellulose, ethyl cellulose, hydroxypropylcelullose, hydroxyethylcellulose, carboxymethylcellullose, hydroxypropyl methylcellulose and mixtures thereof.

In an embodiment, the composition of the present invention is one wherein the hydrophilic matrix forming agent comprises hydroxypropyl methylcellulose. In an embodiment, the composition of the present invention is one wherein the hydrophilic matrix forming agent comprises hydroxypropyl methylcellulose having methoxy moiety content from 15% to 30% by weight of the weight of the hydroxypropylemethylcellulose; preferably from 19% to 24% by weight of the weight of the hydroxypropylemethylcellulose. In an embodiment, the composition of the present invention is one wherein the hydrophilic matrix forming agent comprises hydroxypropylmethylcellulose having hydroxypropyl moiety content from 5% to 15% by weight of the weight of the hydroxypropylemethylcellulose; preferably from 7% to 12% by weight of the weight of the hydroxypropylemethylcellulose. Measurement of the content of the methoxy moiety and hydroxypropyl moiety can be performed by any method known in the art. In a particular embodiment, the hydrophilic matrix forming agent is hydroxypropyl methylcellulose K100M.

In an embodiment, the composition of the present invention is one wherein the hydrophilic matrix forming agent comprises hydroxypropylmethylcellulose having an apparent viscosity from 65000 mPa·s to 150000 mPa·s; preferably from 75000 mPa·s to 140000 mPa·s. The term "apparent viscosity" refers to the resistance of a fluid to shear, also called dynamic or shear viscosity and defined mathematically as a stress-to-shear rate quotient. Measurement of the apparent viscosity can be performed by any method known in the art. Usually, the viscosity is measured by using devices such as rotational viscometers or rheometers which measure the torque exerted on an axis in contact with the sample when it is rotated at a precisely controlled angular velocity. Converting torque and velocity to stress and share rate respectively is straightforward by multiplication by calibration constants. In the present invention, viscosity measurements are performed using a solution of 2% by weight of hydroxypropylmethylcellulose in water at 20° C. using a TA Instruments rheometer fitted with a cone-plate measuring system and applying a cycle of successive increase of the shear rate from 0 to 150 s$^{-1}$ and then decrease from 150 to 0 s$^{-1}$.

In an embodiment, the composition of the present invention is one wherein the hydrophilic matrix forming agent comprises one or more noncellulose polysaccharides selected from the group consisting of carrageenan; amylose sulfate; xylan sulfate; galactomannan; guar gum; carob gum; gum arabic; sterculia gum; agar; alginic acid, a salt of alginic acid; and a mixture thereof. In an embodiment, the composition of the present invention is one wherein the hydrophilic matrix forming agent comprises carrageenan; preferably carrageenan selected from the group consisting of lambda-carrageenan, iota carrageenan, kappa-carrageenan and mixtures thereof. In an embodiment, the composition of the present invention is one wherein the one or more hydrophilic matrix forming agent is lambda-carrageenan. In a particular, the composition of the present invention is one wherein the one or more hydrophilic matrix forming agent is lambda-carrageenan viscarin PH 209.

In an embodiment, the composition of the present invention comprises two or more hydrophilic matrix forming agents. In a particular embodiment, the composition of the present invention comprises two hydrophilic matrix forming agents. In an embodiment, the composition of the present invention is one wherein the one or more hydrophilic matrix forming agents comprises a mixture of hydroxypropylmethylcellulose and carrageenan.

In an embodiment, the composition of the present invention is one wherein the hydrophilic matrix forming agents comprises a mixture of hydroxypropylmethylcellulose and carrageenan wherein the weight ratio between the hydroxypropylmethylcellulose and carrageenan is from 3:1 to 12:1; preferably from 5:1 to 11:1; more preferably from 6:1 to 10:1. In a particular embodiment, the composition of the present invention is one wherein the hydrophilic matrix forming agents comprises a mixture of hydroxypropylmethylcellulose and carrageenan wherein the weight ratio between the hydroxypropylmethylcellulose and carrageenan is 9:1.

The compositions of the present invention comprise one or more pharmaceutically acceptable excipients or carriers. The term "pharmaceutically acceptable excipients or carriers" refers to that excipients or carriers suitable for use in the pharmaceutical technology for preparing compositions with medical use.

The oral solid compositions of the invention can be formulated in any form that includes any single unit dosage form and any multiple unit dosage forms. The term "single unit" encompasses one entity such as a single tablet, a single granule, and a single pellet. The term "single unit dosage form" defines a dosage form which consists only of one unit which contains the effective amount of betahistine. The term "multiple unit dosage form" defines a dosage from which consists of more than one unit which contains the effective amount of betahistine. Usually the multiple unit dosage forms are based on subunits such as granules, pellets or minitablets. They are usually delivered in hard gelatine capsules or transformed into tablets. Thus, it is also part of the invention a unit dosage from which comprises the composition of the present invention. In an embodiment, the unit dosage from which comprises the composition of the present invention is a single unit dosage form. In an embodiment, the unit dosage from which comprises the composition of the present invention is a multiple unit dosage form.

The appropriate excipients and/or carriers, and their amounts, can readily be determined by those skilled in the art according to the type of formulation being prepared.

In an embodiment, the composition of the present invention comprises: an amount of betahistine, or of a pharmaceutically acceptable salt thereof, equivalent to 48 mg of betahistine dihydrochloride; from 20 to 85% by weight of one or more of the hydrophilic matrix forming agent as defined in above; from 20 to 40% by weight of one or more diluents; from 0.1 to 15% by weight of one or more stabilizers; optionally from 0.1 to 15% by weight of one or more binders; optionally from 0.1 to 10% by weight of one or more glidants; and optionally from 0.1 to 10% by weight of one or more lubricants; being the sum of the ingredients 100% by weight.

In an embodiment, the composition of the present invention comprises: an amount of betahistine, or of a pharmaceutically acceptable salt thereof, equivalent to 48 mg of betahistine dihydrochloride; from 35 to 65%, preferably from 40 to 60%, more preferably from 45 to 55%, even more preferably from 50 to 55%, by weight of one or more of the hydrophilic matrix forming agent as defined in above; from 25 to 35%, preferably from 28 to 30%, by weight of one or more diluents; optionally, from 0.5 to 5%, preferably from 1 to 2%, by weight of one or more binders; preferably from 1 to 10%, more preferably from 5 to 7%, by weight of one or more stabilizers; optionally from 0.5 to 5%, preferably from 1 to 3%, by weight of one or more glidants; and optionally from 0.5 to 5%, preferably from 1 to 3%, by weight of one or more lubricants; being the sum of the ingredients 100% by weight.

The terms "filler" and "diluent" have the same meaning and are used interchangeably. They refer to any pharmaceutically acceptable excipient or carrier (material) that fill out the size of a composition, making it practical to produce and convenient for the consumer to use. Materials commonly used as filler include calcium carbonate, calcium phosphate, dibasic calcium phosphate, tribasic calcium sulfate, calcium carboxymethyl cellulose, cellulose, cellulose products such as microcrystalline cellulose and its salts, dextrin derivatives, dextrin, dextrose, fructose, lactitol, lactose, starches or modified starches, magnesium carbonate, magnesium oxide, maltitol, maltodextrins, maltose, mannitol, sorbitol, starch, sucrose, sugar, xylitol, erythritol and mixtures thereof. In an embodiment, the composition of the invention is one wherein the pharmaceutically acceptable excipients or carriers comprises one or more filler; preferably comprises microcrystalline cellulose. In an embodiment, the composition of the invention is one wherein the pharmaceutically acceptable excipients or carriers comprise one or more filler, preferably microcrystalline cellulose, in an amount from 20 to 40%, preferably from 25 to 35%, more preferably from 28 to 30%, by weight of the composition.

The term "stabilizer" refers to any substance that slows or retards the degradation or alteration of active ingredient. Examples of appropriate stabiliser agents for the present invention include, but it is not limited to, alpha-hydroxyl carboxylic acid such as lactic acid, tartaric acid or citric acid. In an embodiment, the composition of the invention is one wherein the pharmaceutically acceptable excipients or carriers comprises one or more stabilizer; preferably comprises citric acid. The compositions of the present invention that comprise citric acid as a stabilizer agent are especially advantageous, because they exhibit a higher stability. In an embodiment, the composition of the invention is one wherein the pharmaceutically acceptable excipients or carriers comprise one or more stabilizer in an amount from 0.1 to 15%, preferably from 1 to 10%, more preferably from 5 to 7% by weight of the composition.

The term "binder" refers to any pharmaceutically acceptable compound having binding properties. Materials commonly used as binders include povidone such as polyvinylpyrrolidone K30, methylcellulose polymers, hydroxyethyl cellulose, hydroxypropyl cellulose, L-hydroxypropyl cellulose (low substituted), hydroxypropylmethyl cellulose (HPMC), sodium carboxymethyl cellulose, carboxymethylene, carboxymethylhydroxyethyl cellulose and other cellulose derivatives, starches or modified starches and mixture thereof. In an embodiment, the composition of the invention is one wherein the pharmaceutically acceptable excipients or carriers comprise one or more binder; preferably comprise polyvinylpyrrolidone, for instance polyvinylpyrrolidone K30. In an embodiment, the composition of the invention is one wherein the pharmaceutically acceptable excipients or carriers comprise one or more binder in an amount from 0.1 to 15%, preferably from 0.5 to 5%, more preferably from 1 to 2% by weight of the composition.

The term "glidant" refers to a substance which improves the flow characteristics of powder mixtures in the dry state. Materials commonly used as a glidant include magnesium stearate, colloidal silicon dioxide or talc. In an embodiment, the composition of the invention is one wherein the pharmaceutically acceptable excipients or carriers comprises one or more glidant; preferably comprises colloidal silicon dioxide. In an embodiment, the composition of the invention is one wherein the pharmaceutically acceptable excipients or carriers comprise one or more glidant in an amount from 0.1 to 10%, preferably from 0.5 to 5%, more preferably from 1 to 3% by weight of the composition.

The term "lubricant" refers to a substance that prevents composition ingredients from clumping together and from sticking to the tablet punches or capsule filling machine and improves flowability of the composition mixture. Materials commonly used as a lubricant include sodium oleate, sodium stearate, sodium benzoate, sodium stearate, sodium chloride, stearic acid, sodium stearyl fumarate, calcium stearate, magnesium stearate, magnesium lauryl sulfate, sodium stearyl fumarate, sucrose esters or fatty acid, zinc, polyethylene glycol, talc and mixtures thereof. The presence of a lubricant is particularly preferred when the composition is a tablet to improve the tableting process.

In an embodiment, the composition of the invention is one wherein the pharmaceutically acceptable excipients or carriers comprise one or more lubricant; preferably comprise a mixture of sodium stearyl fumarate and talc, preferably in a ratio 1:1. In an embodiment, the composition of the invention is one wherein the pharmaceutically acceptable excipients or carriers comprise one or more lubricant in an amount from 0.1 to 10%, preferably from 0.5 to 5%, more preferably from 1 to 3% by weight of the composition.

Additionally, the compositions of the present invention may contain other ingredients, such as colorants, disintegrants, and other components known in the state of the art for use in oral solid formulations.

In an embodiment, the composition of the present invention comprises: an amount of betahistine, or of a pharmaceutically acceptable salt thereof, equivalent to 48 mg of betahistine dihydrochloride; from 20 to 85% by weight of a mixture of hydroxypropylmethylcellulose and carrageenan as defined in above, preferably in a weight ratio 3:1 to 12:1; from 20 to 40% by weight of microcrystalline cellulose; from 0.1 to 15% by weight of citric acid; optionally, from 0.1 to 15% by weight of one or more polyvinylpyrrolidone; optionally from 0.1 to 10% by weight of colloidal silicon dioxide, preferably in a weight ratio 1:2 to 2:1; and optionally from 0.1 to 10% by weight of a mixture of sodium stearyl fumarate and talc as defined above, preferably in a weight ratio 1:1; being the sum of the ingredients 100% by weight.

In an embodiment, the composition of the present invention comprises: an amount of betahistine, or of a pharmaceutically acceptable salt thereof, equivalent to 48 mg of betahistine dihydrochloride; from 35 to 65%, more preferably from 40 to 60%, more preferably from 45 to 55%, even more preferably from 50 to 55% by weight of a mixture of hydroxypropylmethylcellulose and carrageenan as defined above, preferably in a weight ratio 3:1 to 12:1; preferably from 5:1 to 11:1; more preferably from 6:1 to 10:1, and even more preferably 9:1; from 25 to 35%, more preferably from 28 to 30%, by weight of microcrystalline cellulose; optionally, from 0.5 to 5%, preferably from 1 to 3% by weight of polyvinylpyrrolidone; from 1 to 10%, preferably from 5 to 7% by weight of citric acid; optionally from 0.5 to 5%, preferably from 1 to 3% by weight of colloidal silicon dioxide; and optionally from 0.5 to 5%, preferably from 1 to 3% by weight of a mixture of sodium stearyl fumarate and talc as defined above, preferably in a weight ratio 1:1; wherein the sum of the ingredients is 100% by weight.

In a preferred embodiment, the composition of the present invention comprises: 48 mg of betahistine dihydrochloride; from 50 to 55% by weight of a mixture of hydroxypropylmethylcellulose and carrageenan in a weight ratio 9:1; from 28 to 30%, by weight of microcrystalline cellulose; from 1 to 2% by weight of polyvinylpyrrolidone; from 5 to 7% by weight of citric acid; from 1 to 3% by weight of colloidal silicon dioxide; and from 1 to 3% by weight of a mixture of sodium stearyl fumarate and talc in a weight ratio 1:1; wherein the sum of the ingredients is 100% by weight.

Another aspect of the invention is a process for the preparation of the compositions of the present invention as defined above. The compositions of the present invention can be prepared according to methods well known in the state of the art. The appropriate method and conditions can readily be determined by those skilled in the art according to the type of formulation being prepared.

In an embodiment, the composition is in form of a tablet. In an embodiment, the process for preparation of the composition of the invention in form of a tablet as defined above comprises a wet granulation tablet. The process for the manufacturing of these compositions comprises any method known in the art which comprises a wet granulation step. In an embodiment, the process for preparation of the composition as defined above comprises: (a) preparing a solution of betahistine or a pharmaceutically acceptable salt thereof in a polar solvent selected from the group $(C_1$-$C_4)$alkyl-CO—$(C_1$-$C_4)$alkyl, $(C_1$-$C_4)$alky)-COO—$(C_1$-$C_4)$alkyl, water and mixture thereof; (b) sifting and mixing one or more diluents, one or more stabilizers and optionally one or more binders to obtain a mixture; (c) granulating the mixture of step (b) by the addition of the solution of step (a) to obtain wet granules; (d) drying the wet granules obtained in step (c) to obtain dried granules; (e) mixing the dried granules obtained in step (d) with one or more hydrophilic matrix forming agents to obtain a mixture; (f) optionally, blending the mixture obtained in step (e) with one or more of the excipients or carriers selected from the group consisting of glidant and lubricant to obtain a mixture; (g) compressing the mixture obtained in step (f) to form tablets, and (h)

optionally, coating the tablets obtained in step (g). This process is advantageous because it allows preparing a stable composition comprising an amount of betahistine, or of a pharmaceutically acceptable salt thereof, equivalent to 48 mg of betahistine dihydrochloride, together with one or more pharmaceutically acceptable excipients or carriers that has the targeted dissolution profile. Particularly, this process comprises a wet granulation step which allows the preparation of intermediate granules comprising the betahistine active ingredient together with one or more diluents, one or more stabilizers and optionally one or more binders. This process step enhances the stability of the active ingredient and avoids the absorption or attraction of moisture or water molecules from the air. This process in especially advantageous in the present case, since betahistine, especially betahistine dihydrochloride, is a highly water-soluble and hygroscopic active ingredient.

In an embodiment, step (a) of the process for preparation of the composition of the invention is performed at room temperature. In an embodiment, step (a) of the process for preparation of the composition of the invention is performed in a rapid mixer granulator.

In an embodiment, step (b) of the process for preparation of the composition of the invention is performed at room temperature. In an embodiment, step (a) of the process for preparation of the composition of the invention is performed in a rapid mixer granulator.

In an embodiment, step (c) of the process for preparation of the composition of the invention is performed at room temperature, preferably at a temperature from 20° C. to 25° C. In an embodiment, step (c) of the process for preparation of the composition of the invention is performed in any granulator mixer equipment; preferably in a rapid mixer granulator.

In an embodiment, step (d) of the process for preparation of the composition of the invention is performed at a temperature from 45° C. to 70° C.; preferably from 50° C. to 60° C. In an embodiment, step (d) of the process for preparation of the composition of the invention is performed until the water content (LOD) is equal to or less than 2% by weight.

In an embodiment, steps (e) and (f) of the process for preparation of the composition of the invention is performed at room temperature, preferably is performed at a temperature from 20° C. to 25° C.

In an embodiment, the compressing step (g) of the process for preparation of the composition of the invention is performed using compression machine equipment. In an embodiment, the compressing step (g) of the process for preparation of the composition of the invention is performed at a compression force 150N to 220 N; particularly at 180 N to obtain tablets having a weight about 700 to 900 mg, preferably having a weight about 750 to 800 mg, more preferably having a weight about 785 mg.

All the embodiments disclosed above for the non-pulsatile 24 hours prolonged-release oral solid composition of the present invention also apply for the process for its preparation.

In an embodiment, the composition is in form of hard gelatine capsules. In an embodiment, the process for preparation of the composition of the invention can be performed by any method known in the state of the art for preparing hard gelatine capsules. Typically, the process comprises mixing the betahistine, or the pharmaceutically effective amount, with the appropriate pharmaceutically acceptable excipients or carriers followed by filling the hard gelatine capsules manually, or by using semiautomatic or automatic machines.

In an embodiment, the composition is in form of pellets. In an embodiment, the process for preparation of the composition of the invention can be performed by any method known in the state of the art for preparing pellets. Typically, pellets can be prepared by extrusion-spheronizating process or by layering an inner core.

The non-pulsatile 24 hours prolonged-release oral solid composition may be defined by its preparation process as defined above and therefore, the non-pulsatile 24 hours prolonged-release oral solid composition of the invention obtainable by the process of the invention is considered part of the invention. For the purposes of the invention, the expressions "obtainable", "obtained" and equivalent expressions are used interchangeably, and in any case, the expression "obtainable" encompasses the expression "obtained".

All the embodiments disclosed above for the non-pulsatile 24 hours prolonged-release oral solid composition of the present invention, as well as for the process for its preparation, also apply for the non-pulsatile 24 hours prolonged-release oral solid composition obtainable by the process for preparation.

The third aspect of the invention relates to a non-pulsatile 24 hours prolonged-release oral solid composition of the present invention as defined above for use as a medicament. In an embodiment, the invention relates to the non-pulsatile 24 hours prolonged-release oral solid composition of the present invention as defined above for use as a medicament wherein the medicament is administered once-daily.

The fourth aspect of the invention relates to a non-pulsatile 24 hours prolonged-release oral solid composition of the present invention as defined above for use in the treatment of a vestibular (inner ear) disease or condition. This aspect could be also formulated as the use of a non-pulsatile 24 hours prolonged-release oral solid composition of the present invention as defined above for the preparation of a medicament for the prophylaxis and/or treatment of a vestibular disease or condition. It also relates to a method for the prophylaxis and/or treatment of a mammal suffering, or susceptible to suffer, from a vestibular disease or condition, wherein the method comprises administering to said mammal the non-pulsatile 24 hours prolonged-release oral solid composition of the present invention as defined above. In an embodiment, the vestibular disease or condition refers to Ménière's disease or disorder, symptoms of which may include vertigo, tinnitus, hearing loss and nausea.

In an embodiment, a non-pulsatile 24 hours prolonged-release oral solid composition of the present invention as defined above for use in the treatment of a vestibular disease or condition, preferably for use in the treatment of Ménière's disease, wherein the treatment comprises once-daily administration of the non-pulsatile 24 hours prolonged-release oral solid composition.

All the embodiments disclosed above for the non-pulsatile 24 hours prolonged-release oral solid composition of the present invention also apply for the non-pulsatile 24 hours prolonged-release oral solid composition limited by its use.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

Pharmacokinetic measured molecule: betahistine metabolite 2-PAA: As per the European Summary of Product Characteristics of Betahistine dihydrochloride tablets (Betaserc® tablets) orally administered betahistine is readily and almost completely absorbed from all parts of the gastro-intestinal tract. After absorption, the drug is rapidly and almost completely metabolized into 2-pyridylacetic acid (2-PAA). The absolute bioavailability of betahistine, dosed as the immediate release tablet or the orodispersible tablet, is estimated to be around 1% due to its very high first pass metabolism. Plasma levels of betahistine are very low. The majority of pharmacokinetic analyses are therefore based on 2-PAA measurements in plasma and urine, which is supposed to be a surrogate marker for Betahistine bioanalysis. Hence, bioequivalence based on the metabolite 2-pyridylacetic acid (2-PAA) is considered acceptable by the Regulatory Medicinal Agencies. Likewise, it is expected that pharmacokinetic analyses based on plasma levels of low-available betahistine parent drug would provide similar bioequivalence results.

Example 1

Compositions

The components of an example of the prolonged release composition of the present invention in form of a tablet are shown in Table 1, wherein the amounts of the components are expressed in weight percent:

TABLE 1

| | | Example 1 | |
|---|---|---|---|
| Name | Function | Mg/tablet | (% w/w) |
| Betahistine dihydrochloride | Active ingredient | 48 | 6.11 |
| Cellulose microcrystalline | diluent | 230 | 29.30 |
| Citric acid anhydrous | Stabilizer | 50 | 6.37 |
| Polyvinylpyrrolidone K30 | binder | 12 | 1.53 |
| Hydroxypropylmethylcellulose K100M premium CR | Hydrophilic matrix forming agents | 374 | 47.64 |
| Lambda carrageenan[(1)] | | 40 | 5.10 |
| Colloidal anhydrous silica | Glidant | 15 | 1.91 |
| Talc | lubricant | 8 | 1.02 |
| Sodium stearyl fumarate | lubricant | 8 | 1.02 |
| | Total weight | 785 | 100 |

[(1)]Commercially available as viscarin PH 209

The composition of the invention of Example 1 as defined in Table 1 was performed following the process disclosed below using the amounts of the ingredients specified in Table above:

(a) betahistine was dissolved in a sufficient amount of purified water for the completely dissolution of betahistine with continuous stirring till clear solution is obtained;

(b) a mixture of the diluent, the stabilizer and the binder were stirred and sifted through a sieve of 40 mesh and loaded in a rapid mixer granulator (RMG);

(c) granulating the mixture obtained in step (b) by the addition of the solution obtained in step (a). The resultant mixture was stirred for 5 minutes to obtain wet granules;

(d) wet granules obtained in step (c) were dried into a dryer at a temperature of 55±10° C. until the content of water (LOD—loss on drying) reached 2.0%. Then, dried granules were sifted through a sieved of 40 mesh and blended for 5 minutes at 16 rpm;

(e) a mixture of the hydrophilic matrix forming agents were prepared and sifted through a sieve of 40 mesh; and this mixture was added to the dried granules obtained in step (d) and mixed in a blender for 20 minutes at 16 rpm;

(f) to the resultant blend obtained in step (e) the glidants and the lubricants previously sifted through a sieve of 40 mesh was added; and the resultant mixture was blended for 5 minutes at 16 rpm;

(g) the resultant mixture obtained in step (f) was compressed using an 18×10 mm oval concave shape punch to obtain a tablet having a hardness from 150 N to 220 N.

The obtained tablet showed a total impurity content below 0.15%, as measured by HPLC method.

The conditions of the HPLC method is as follows:
Flux: 1.3 mL/min
Column: Peerless basic C18 (250 mm×4.6 mm), 4μ;
  Make: Chromatopak
Porous size of the column: 4μ
Phases: Mobile phase-A: [(Buffer:Methanol:Acetonitrile): (45:40:15)].
  Mobile phase-B: [(Buffer:Acetonitrile): (45:55)].
Detection wavelength: 260 nm
Injection volume: 50 μL
Column temperature: 25° C.
Gradient:

| Time (Minutes) | Mobile phase-A (% v/v) | Mobile phase-B (% v/v) |
|---|---|---|
| 0.0 | 100 | 0 |
| 6.0 | 100 | 0 |
| 48.0 | 0 | 100 |
| 53.0 | 0 | 100 |
| 54.0 | 100 | 0 |
| 70.0 | 100 | 0 |

Example 2

Dissolution Test

The dissolution profile of the prolonged release tablet composition of Example 1 having 48 mg of betahistine dihydrochloride was measured at different pH conditions.
Conditions of the dissolution bath
Paddle speed: 100 rpm
Temperature of dissolution medium: 37° C.±0.5° C.
Dissolution Medium: Conditions A: 0.1N HCl
  Conditions B: pH 4.5 with acetate buffer
  Conditions C: pH 6.8 with phosphate buffer
Vessel volume: 900 mL
Time point (hours): 0.5, 1, 4, 8, 16 and 24.
no of units: 6
Method:
To the set dissolution apparatus having a 900 mL of dissolution medium as defined above to each of six glass vessels and under the above mentioned conditions, a tablet of the test sample was added into each basket lower down hood, taking care to exclude the air bubbles from the surface of the tablet and immediately start the apparatus.

After that, at each time point, 10 mL of the test sample from each of six glass vessels were withdrawn. Then, 2 mL of the aliquot of the test sample were transferred from the collected sample to a single test tube, wherein it was mixed and filtered through 0.45μ polyvinylidene fluoride filter (PVDF filter). Further, the withdrawn volume at each time point is replaced by adding an equal quantity of fresh dissolution medium at 37° C.±0.5° C.

Conditions of the chromatographic analysis
Instrument: High Performance Liquid Chromatograph equipped with auto sampler, UV detector and inbuilt thermostat column compartment.
Column: Zorbax Eclipse XDB C18 (150 mm×4.6 mm), 5μ, Make: Agilent or equivalent
Flux: 1.5 mL/min
Column temperature: 35° C.
Injection volume: 10 μL
Wavelength: 260 nm
run time 3.5 min
Retention Time of betahistine: about 2.7 min
Mobil Phase: mixing 600 volumes of Buffer 1 and 400 volumes of Acetonitrile, filtered through 0.45μ Nylon filter, and Degassed by sonication.

Buffer 1: dissolving 4.6 g of Sodium dihydrogen orthophosphate monohydrate ($NaH_2PO_4.H_2O$) in 900 mL of water; adding 0.66 g of hexylamine and mixing. Then, the pH is adjusted to 2.7±0.05 by the addition of 10% v/v of orthophosphoric acid. Finally, making up to 1000 mL with water and mixing; and adding 2.7 g of sodium dodecyl sulfate by gentle stirring until dissolution.

Betahistine Internal Reference standard stock preparation: Transferring 33.3 mg of Betahistine dihydrochloride working standard into a 50 mL volumetric flask; adding 40 mL of water and sonicated until dissolution. Finally, diluting to volume with water and mixing for having a final concentration of 0.666 mg/mL.

Betahistine Internal Standard preparation: Diluting 4.0 mL of the Betahistine Internal Reference standard stock preparation to 50 mL with dissolution medium as defined above and mixing until having a final concentration of 0.053 mg/mL.

Method
System suitability: Equilibrate the column with mobile phase as defined above at the above specified condition until stable base line obtained. Inject six replicate injections of standard preparation into the liquid chromatograph and record the chromatograms. Measure the response for the Betahistine peak.

In the chromatogram obtained with standard preparation:
% Relative standard deviation for Betahistine peak area of six replicate injections should not be more than 2.00.
Theoretical plates for Betahistine peak should not be less than 1000.
Tailing factor for Betahistine peak should be between 0.80 and 2.00.

Procedure: Inject separately single injection each of dissolution medium as blank and test sample into the liquid chromatograph and record the chromatograms. Measure the response for the Betahistine peak. Calculate the dissolved quantity of Betahistine Dihydrochloride in percentage of label claim from mean peak areas of standard preparation and peak area of the test sample and percentage potency of working standard used.

Calculation: % of Dissolved Betahistine dihydrochloride $$\frac{Au}{As} \times \frac{W_1}{50} \times \frac{4}{50} \times \frac{900}{L.C.} \times P$$

Wherein,
Au=Peak area due to Betahistine obtained with sample preparation.
As=Mean peak area due to Betahistine obtained with standard preparation.
$W_1$=Weight of Betahistine dihydrochloride working standard taken in mg.
L.C.=Label claim of Betahistine dihydrochloride in mg/tablet.
P=Potency of Betahistine dihydrochloride working standard in percentage on as is basis.

Calculate the correction factor for the percentage drug loss at the end of each time point. Add this correction factor to the value of % dissolved obtained in the succeeding time point.

$$\text{Correction factor:} \frac{\text{Withdrawn volume} \times \% \text{ dissolved (\% label claim) at each time point}}{\text{Volume of dissolution medium}}$$

For 0.5 hr point: % dissolved in $0.5^{th}$ hr.
For 1 hr point: Correction factor of $0.5^{th}$ hr+% dissolved in $1^{st}$ hr.
For 4 hrs point: Correction factor of ($0.5^{th}$ hr+$1^{st}$ hr)+% dissolved in $4^{th}$ hrs.
For 8 hrs point: Correction factor of ($0.5^{th}$ hr+$1^{st}$ hr+$4^{th}$ hrs)+% dissolved in $8^{th}$ hrs.
For 16 hrs point: Correction factor of ($0.5^{th}$ hr+$1^{st}$ hr+$4^{th}$ hrs+$8^{th}$ hrs)+% dissolved in $16^{th}$ hrs.
For 24 hrs point: Correction factor of ($0.5^{th}$ hr+$1^{st}$ hr+$4^{th}$ hrs+$8^{th}$ hrs+$16^{th}$ hrs)+% dissolved in $24^{th}$ hrs.

Results

The weight percept of betahistine dihydrochloride released from the composition of Example 1 of the present invention submitted to the different dissolution conditions at time points from 0.5 hours to 24 hours; as well as the relative standard deviation is shown in Table 2:

TABLE 2

| | Media | | | | | |
|---|---|---|---|---|---|---|
| | Conditions A | | Conditions B | | Conditions C | |
| Time Points (Hours) | Betahistine release (%) | RSD (%) | betahistine release (%) | RSD (%) | betahistine release (%) | RSD (%) |
| 0.5 | 19 | 1.35 | 18 | 2.75 | 18 | 0.55 |
| 1 | 27 | 1.14 | 25 | 2.73 | 25 | 0.79 |
| 2 | 39 | 1.31 | 37 | 2.32 | 37 | 0.73 |
| 4 | 56 | 1.14 | 53 | 3.03 | 54 | 0.58 |
| 6 | 69 | 1.21 | 66 | 2.62 | 66 | 0.52 |
| 8 | 77 | 1.22 | 74 | 2.47 | 75 | 0.77 |
| 10 | 84 | 1.28 | 81 | 2.39 | 82 | 0.82 |
| 12 | 89 | 1.32 | 85 | 2.49 | 88 | 0.86 |
| 16 | 95 | 1.44 | 91 | 2.81 | 95 | 0.96 |
| 20 | 98 | 1.56 | 95 | 2.67 | 98 | 1.39 |
| 24 | 100 | 1.7 | 98 | 2.56 | 102 | 1.39 |

The dissolution profile results in Table 2 showed that the composition of betahistine dihydrochloride 48 mg of the present invention has the required dissolution profile regardless the pH. It means that up to 30% of betahistine is dissolved in 1 hour; from 35% to 45% of betahistine is dissolved in 2 hours; from 46% to 60% of betahistine is dissolved in 4 hours; from 61% to 80% of betahistine is dissolved in 8 hours; from 81% to 97% of betahistine is dissolved in 16 hours; and from 98% to 100% by weight of betahistine is dissolved in 24 hours.

Furthermore, the target dissolution profile showed in Table 2 was maintained even when the dissolution test was performed in the presence of up to 40% of ethanol in 0.1N HCl media up to 2 hours.

Thus, the compositions of the present invention are advantageous because they show a pH independent solubility and they avoid the dose-dumping effect (even in the presence of ethanol) at the early hours (between 0 to 2 hours). Furthermore, the compositions of the present invention also allow controlling the release of the betahistine dihydrochloride even when the dissolution of betahistine dihydrochloride has already started (i.e. between 4 to 16 hours) without the need of additional controlled release layers or coatings. It is also advantageous because the composition of the present invention allows maintaining the therapeutically effective amount of betahistine for 24 hours and even at a prolonged period of time after several days (multiple dose steady-state) with once a day dosing. Also, the composition of the invention leads to improved tolerability by means of lesser fluctuations between the peak and trough plasma concentrations due to the steady-state release of the drug over a prolonged period of time.

Example 3

Bioavailability Test

The bioavailability of the prolonged release compositions of the present invention was studied.

A. Design of the study

The trial was carried out as an open label, balanced, randomized, two-treatment, two sequence, two-period, crossover, oral dose, comparative bioavailability study in normal, healthy, adult, human subjects under fed conditions B. Volunteers Sufficient number of healthy, adult, human volunteers was screened with their consent to enrol 16 subjects in the study, and which further complied with the following criteria of inclusion:

Healthy, adult, human subjects between 18 and 45 years of age (both inclusive).

Having a Body Mass Index (BMI) between 18.5 and 30.0 (both inclusive), calculated as weight in kg/height in m$^2$.

Not having significant diseases or clinically significant abnormal findings during screening, medical history, clinical examination, laboratory evaluations, 12 lead ECG, and chest X-ray recordings (postero-anterior view).

Able to understand and comply with the study procedures, in the opinion of the Investigator.

Volunteer who is a Non-smoker and Non-Alcoholics.

Able to give voluntary written informed consent for participation in the study.

In case of female subjects:

Surgically sterilized at least 6 months prior to study participation; or         If of child bearing potential is willing to use a suitable and effective double barrier contraceptive method or intra uterine device during the study, and         Serum pregnancy test must be negative.

C. Samples

The samples used in the bioavailability test are the following:

a) Test sample: The prolonged release composition of Example 1 in form of tablet packaged inside an Aluminium-Aluminium blister having 48 mg of betahistine dihydrochloride; and     b) Reference Test: Betaserc® 24 mg in form of tablets.

D. Test Method

The test and reference samples were administered to the subjects in sitting posture with 240±02 mL of drinking water at ambient temperature. The tablet to be swallowed has to be whole without chewing or crushing.

For Test Sample:

After overnight fasting of at least 10 hours, subjects were served standardized high fat high calorie vegetarian breakfast, which they were required to consume within 30 minutes. The test sample was to be administered once at 30 minutes after serving standardized high fat high calorie vegetarian breakfast.

For Reference Sample:

After overnight fasting of at least 10 hours, subjects were served standardized high fat high calorie vegetarian breakfast, which they are required to consume within 30 minutes. The first dose of reference sample product was administered at 30 minutes after serving standardized high fat high calorie vegetarian breakfast. Further, again standardized high fat high calorie vegetarian breakfast was served at 11.5 hours after first dose, which they were required to consume within 30 minutes. Second dose was administered at 12.00 hours (interval between two consecutive doses is 12 hours±5 minutes).

Sampling

At initial time and at each hour (i.e. each time points) after administration, blood was collected.

Blood samples were collected through an indwelling intravenous cannula (Venflon) placed in a forearm vein of the subjects. Intravenous indwelling cannula was kept in situ as long as possible by injecting 0.5 mL of normal saline solution to prevent cannula from clogging for collection of all the blood samples during housing.

The blood samples were centrifuged at 3000·100 rcf for 5 minutes below 10° C. to separate plasma. The separated plasma was transferred to pre-labelled polypropylene tube and stored upright in a box containing dry ice or in a freezer at a temperature −65±10° C. for interim storage as required.

Finally the samples were transferred by keeping them in dry ice box and stored in bioanalytical freezer at −65±10° C. until completion of analysis Determinations The method involved the measurement of the plasma concentration of the betahistine metabolite 2-pyridylacetic acid (2-PAA) for 24 hours at predetermined time points.

Mean plasma concentration of 2-pyridylacetic acid metabolite were determined.

Figure 1:
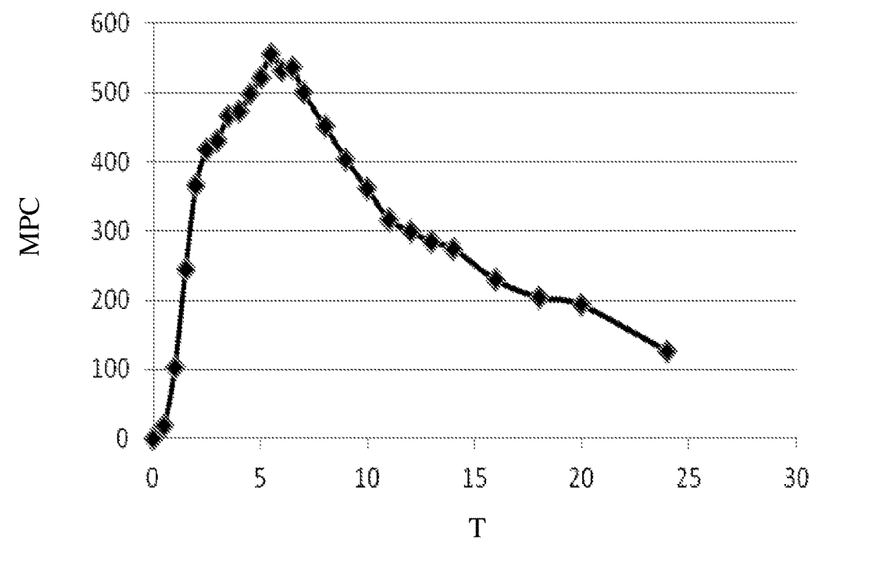
FIG. 1 shows the mean plasma concentration (MPC) for 24 hours after a unique oral administration of the composition of Example 1 of the present invention having 48 mg of betahistine dihydrochloride. MPC stands for mean plasma concentration (ng/mL) and T refers to time expressed in hours.

Values of 2-pyridylacetic acid concentration after once-daily administration of the test sample of the present invention and after twice-daily administration of the reference sample were summarized in Table 3. Further, the plasma concentration-time profile after the twice-daily administration of the test sample is shown in FIG. 1.

TABLE 3

| Time points (h) | Mean plasma concentration of 2-pyridylacetic acid after once-daily intake of the composition of the invention (ng/mL) | Time points (h) | Mean plasma Concentration of 2-pyridylacetic acid after twice-daily intake of betaserc (ng/mL) |
|---|---|---|---|
| 1 | 0 | 0 | 0 |
| 2 | 18.603 | 0.25 | 33.658 |
| 3 | 102.149 | 0.5 | 163.894 |
| 4 | 245.141 | 0.75 | 279.357 |
| 5 | 365.008 | 1 | 389.983 |
| 6 | 418.641 | 1.25 | 484.561 |
| 7 | 430.711 | 1.5 | 520.104 |
| 8 | 467.489 | 1.75 | 535.899 |
| 9 | 472.716 | 2 | 541.278 |
| 10 | 497.257 | 2.5 | 512.795 |
| 11 | 521.026 | 3 | 474.648 |
| 12 | 555.301 | 4 | 405.296 |
| 13 | 531.893 | 6 | 280.773 |
| 14 | 535.699 | 8 | 187.779 |
| 15 | 500.475 | 10 | 122.531 |
| 16 | 450.886 | 12 | 85.617 |
| 17 | 403.466 | 12.25 | 87.553 |
| 18 | 360.009 | 12.5 | 125.143 |
| 19 | 317.407 | 12.75 | 207.204 |
| 20 | 299.445 | 13 | 285.08 |
| 21 | 284.528 | 13.25 | 348.117 |
| 22 | 275.104 | 13.5 | 372.977 |
| 23 | 229.401 | 13.75 | 412.126 |
| 24 | 204.423 | 14 | 436.498 |
|  |  | 14.5 | 504.953 |
|  |  | 15 | 528.722 |
|  |  | 16 | 490.048 |
|  |  | 18 | 408.271 |
|  |  | 20 | 330.138 |

Furthermore, the main pharmacokinetic parameters exhibited after the once-daily administration of the composition of the present invention (Example 1) and the twice-daily administration of the reference sample were measured by means of LC-MS/MS method.

Particularly, the values of the $C_{max}$, $T_{max}$, AUC, $T_{lag}$, $t_{1/2}$, (half life) and $\lambda_z$ (elimination rate constant) as well as the standard deviation (SD) of the test sample and the reference sample were summarized in Table 4.

TABLE 4

| Pharmacokinetic Parameters | Parameters Units | Mean ± SD (untransformed data) | |
|---|---|---|---|
|  |  | Test Sample | Reference Sample |
| $T_{max}^{(a)}$ | H | 5.517 (5.000-7.000) | 13.250 (0.500-18.000) |
| $C_{max}$ | ng/mL | 565.241 ± 50.0996 | 668.300 ± 129.3477 |
| $AUC_{0-t}$ | ng · h/mL | 7187.278 ± 1106.3093 | 7459.269 ± 1276.1453 |
| $AUC_{0-\infty}$ | ng · h/mL | 9042.249 ± 2274.5611 | 8639.921 ± 1581.1539 |
| $\lambda_z$ | 1/h | 0.086 ± 0.0297 | 0.155 ± 0.0286 |
| $t_{1/2}$ | h | 9.086 ± 3.4656 | 4.616 ± 0.7698 |
| AUC_% Extrap_obs | % | 18.573 ± 9.1528 | 13.417 ± 2.9479 |
| $T_{lag}^{(a),(b)}$ |  | 0.000 | — |

$^{(a)}T_{max}$ and $T_{lag}$ are represented in median (min-max) value.
$^{(b)}$calculated for Test formulation only.

The relative bioavailability analyses (i.e. geometric least squares means, ratio, 90% confidence interval, intra subject CV and power) of Test sample vs. Reference sample for betahistine metabolite 2-Pyridylacetic acid were summarized in Table 5:

TABLE 5

| Pharmacokinetic Parameters | Parameters Units | Mean ± SD Test Sample |
|---|---|---|
| $T_{max}^{(a)}$ | H | 5.517 (5.000-7.000) |
| $C_{max}$ | ng/mL | 565.241 ± 50.0996 |
| $AUC_{0-t}$ | ng · h/mL | 7187.278 ± 1106.3093 |
| $AUC_{0-\infty}$ | ng · h/mL | 9042.249 ± 2274.5611 |
| $\lambda_z$ | 1/h | 0.086 ± 0.0297 |
| $t_{1/2}$ | H | 9.086 ± 3.4656 |
| AUC_% Extrap_obs | % | 18.573 ± 9.1528 |
| $T_{lag}^{(a),(b)}$ |  | 0.000 |

$^{(a)}T_{max}$ and $T_{lag}$ are represented in median (min-max) value.
$^{(b)}$calculated for Test formulation only.

The above pharmacokinetic parameters and the values of the mean plasma concentration of the betahistine metabolite 2-pyridylacetic acid shown in Tables above demonstrated that the once-daily administration of the composition of the present invention which contain 48 mg exhibits a lower maximum blood concentration and a higher minimum blood concentration than the twice-daily administration of the reference compound. It is advantageous because improved the tolerability of the active ingredient, and also the efficacy control.

The above mentioned values also showed that the plasma concentration fluctuation has been reduced. This reduction in the plasma fluctuation allows maintaining the plasma therapeutically effective amount of betahistine for 24 hours after once-daily administration, and avoiding the infra-dosing or over-dosing side effects associated with the twice daily administration of an immediate released composition which contains 24 mg of betahistine dihydrochloride (reference sample).

Furthermore, it was surprisingly found that the value of AUC which represents the total drug exposure exhibited after the once-daily administration of the composition of the present invention is bioequivalent to the total drug exposure obtained after twice-daily administration of the immediate-release reference sample. It means that the composition of the present invention has comparable bioavailability, because the rate and extent to which the betahistine dihydrochloride is absorbed from the composition of the invention and becomes available at the site of drug action is the same as the reference sample. Therefore, the once-daily administration of the composition of the present invention can be considered equivalent to twice-daily administration of the immediate-release reference according to the guidelines on modified release formulations of the European medicines Agency (EMA).

In conclusion, the composition of the present invention which comprises betahistine, or a pharmaceutically salt thereof, equivalent to 48 mg of betahistine dihydrochloride allows simplifying the dose posology of betahistine patients by the reduction of daily intakes. It is advantageous because allows reducing the percentage of abandonment by the patient and as a consequence an increase in the treatment effectiveness.

CITATION LIST

1. Kovshel A. Yu. et al, "sustained release betahistine tablets: elaboration of their composition and technology", Pharmacy, 2014, vol. 6, pp. 40.
2. Quality of prolonged release oral solid dosage forms Directive 75/318/EEC October 1992. Section 3AQ19a pp. 167-174.
3. Public Assessment Report of the Medicines Evaluation Board in The Netherlands for betahistine hydrochloride (EU-procedure number: NL/H/1046/01-02/MR; Registration number in the Netherlands: RVG 34738, 34739; 25 Mar. 2008)
4. "Guideline on the pharmacokinetic and clinical evaluation of modified release dosage forms" European medicines Agency (EMA) available on June 2017 in the website EMA/CPMP/EWP/280/96Corr1.

We claim:

1. A non-pulsatile 24 hours prolonged-release oral solid composition comprising an amount of betahistine, or of a pharmaceutically acceptable salt thereof, equivalent to 48 mg of betahistine dihydrochloride, together with one or more pharmaceutically acceptable excipients or carriers, wherein the composition exhibits a dissolution profile according to which:
    up to 30% by weight of betahistine is dissolved in 1 hour;
    from 35% to 45% by weight of betahistine is dissolved in 2 hours;
    from 46% to 60% by weight of betahistine is dissolved in 4 hours;
    from 61% to 80% by weight of betahistine is dissolved in 8 hours;
    from 81% to 97% by weight of betahistine is dissolved in 16 hours; and
    from 98% to 100% by weight of betahistine is dissolved in 24 hours
    wherein the dissolution profile is measured using a USP type I apparatus (basket), placing the composition in 900 mL of phosphate buffer having pH 6.8, at 37° C. and 100 rpm,
    wherein the pharmaceutically acceptable excipients or carriers comprise one or more hydrophilic matrix forming agents, and
    wherein the hydrophilic matrix forming agent is a mixture of hydroxypropylmethylcellulose and carrageenan.
2. The composition according to claim 1, which comprises betahistine dihydrochloride salt.
3. The composition according to claim 1, wherein after an oral single-dose administration of the composition under fed conditions, betahistine or a pharmaceutically acceptable salt thereof, equivalent to 48 mg of betahistine dihydrochloride exhibits a maximum plasma concentration (Cmax) of from 400 ng/ml to 700 ng/ml expressed as plasma concentration of its 2-pyridylacetic acid metabolite.
4. The composition according to claim 1, wherein after an oral single-dose administration of the composition under fed conditions, betahistine, or a pharmaceutically acceptable salt thereof, equivalent to 48 mg of betahistine dihydrochloride exhibits a time to maximum plasma concentration (Tmax) of from 5 h to 7 h expressed as plasma concentration of its 2-pyridylacetic acid metabolite.
5. The composition according to claim 1, wherein after an oral single-dose administration of the composition under fed conditions, betahistine, or a pharmaceutically acceptable salt thereof, equivalent to 48 mg of betahistine dihydrochloride exhibits an area under the time/plasma concentration curve from time 0 to 24 hours (AUC (0-24)) of from 5000 ng·h/ml to 10000 ng·h/ml expressed as plasma concentration of its 2-pyridylacetic acid metabolite.
6. The composition according to claim 1, wherein the weight ratio between the hydroxypropylmethylcellulose and carrageenan is from 3:1 to 12:1.
7. The composition according to claim 1, which comprises:
    an amount of betahistine, or of a pharmaceutically acceptable salt thereof, equivalent to 48 mg of betahistine dihydrochloride;
    from 20 to 85% by weight of hydrophilic matrix forming agent is a mixture of hydroxypropylmethylcellulose and carrageenan;
    from 20 to 40% by weight of one or more diluents;
    from 0.1 to 15% by weight of one or more stabilizers;
    from 0.1 to 15% by weight of one or more binders;
    from 0.1 to 10% by weight of one or more glidants;
    and from 0.1 to 10% by weight of one or more lubricants;
    being the sum of the ingredients 100% by weight.
8. A process for the preparation of the composition as defined in claim 1, which comprises:
    (a) preparing a solution of betahistine or a pharmaceutically acceptable salt thereof in a polar solvent selected from the group (C1-C4)alkyl-CO—(C1-C4)alkyl, (C1-C4)alky)-COO—(C1-C4)alkyl, water and mixture thereof:
    (b) sifting and mixing one or more diluents, one or more stabilizers and optionally one or more binders to obtain a mixture;
    (c) granulating the mixture of step (b) by the addition of the solution of step (a) to obtain wet granules;
    (d) drying the wet granules obtained in step (c) to obtain dried granules;
    (e) mixing the dried granules obtained in step (d) with one or more hydrophilic matrix forming agents to obtain a mixture,
    (f) blending the mixture obtained in step (e) with one or more of the excipients or carriers selected from the group consisting of glidant and lubricant to obtain a mixture;
    (g) compressing the mixture obtained in step (f) to form tablets, and
    (h) coating the tablets obtained in step (g).
9. The composition according to claim 1, wherein the one or more hydrophilic matrix forming agents are in an amount from 35% to 65%, by weight of the total weight of the composition.
10. The composition according to claim 1, wherein the one or more hydrophilic matrix forming agents are in an amount from 40% to 60%, by weight of the total weight of the composition.
11. The composition according to claim 1, wherein the one or more hydrophilic matrix forming agents are in an amount from 45% to 55%, by weight of the total weight of the composition.

12. The composition according to claim 1, wherein the one or more hydrophilic matrix forming agents are in an amount from 50% to 55%, by weight of the total weight of the composition.

\* \* \* \* \*